United States Patent [19]

Friese et al.

[11] Patent Number: 5,423,973
[45] Date of Patent: Jun. 13, 1995

[54] EXHAUST GAS SENSOR AND METHOD OF PRODUCING THE SAME

[75] Inventors: Karl-Hermann Friese, Leonberg; Hans-Martin Wiedenmann, Stuttgart; Helmut Weyl, Schwieberdingen, all of Germany

[73] Assignee: Robert Bosch GmbH, Stuttgart, Germany

[21] Appl. No.: 211,083
[22] PCT Filed: Aug. 27, 1992
[86] PCT No.: PCT/DE92/00714
§ 371 Date: Jun. 20, 1994
§ 102(e) Date: Jun. 20, 1994
[87] PCT Pub. No.: WO93/06472
PCT Pub. Date: Apr. 1, 1993

[30] Foreign Application Priority Data

Sep. 21, 1991 [DE] Germany .............. 41 31 503.0

[51] Int. Cl.⁶ ................................ G01N 27/26
[52] U.S. Cl. ................................ 204/426; 204/427; 204/429
[58] Field of Search ............ 204/421, 424, 425, 426, 204/427, 429; 427/123, 125, 126.2, 126.4, 126.5, 269, 376.1, 376.2, 376.3, 376.6, 419.3

[56] References Cited

U.S. PATENT DOCUMENTS

| | | | |
|---|---|---|---|
| 4,272,349 | 6/1981 | Furutani et al. | 204/428 |
| 4,283,441 | 8/1981 | Haecker et al. | 427/126.2 |
| 4,296,148 | 10/1981 | Friese | 427/125 |

FOREIGN PATENT DOCUMENTS

| | | |
|---|---|---|
| 0159905 | 10/1985 | European Pat. Off. |
| 0369238 | 5/1990 | European Pat. Off. |
| 2656648 | 6/1977 | Germany |
| 2265309 | 11/1977 | Germany |
| 62-14055 | 1/1987 | Japan |
| 1-213567 | 8/1989 | Japan |

*Primary Examiner*—John Niebling
*Assistant Examiner*—Bruce F. Bell
*Attorney, Agent, or Firm*—Spencer, Frank & Schneider

[57] ABSTRACT

An exhaust gas sensor which is exposed to exhaust gas, includes a measuring electrode; and a porous ceramic coating provided on the measuring electrode and comprised of at least two layers, a first porous ceramic layer which is provided on the measuring electrode and at least a second porous ceramic layer which is provided on the first porous ceramic layer and which is directly exposed to the exhaust gas, wherein the first porous ceramic layer contains getter substances for removal of substances that are harmful to the measuring electrode, and wherein the second porous ceramic layer is provided with one of a diffusion resistance or a catalytic effect relative to exhaust gas constituents such that, at the boundary of the first and second porous ceramic layers, a gas composition is present in use which is comprised of one of oxidizable or reducible gas constituents and which sets a control position for the exhaust gas sensor.

5 Claims, 1 Drawing Sheet

EXHAUST GAS SENSOR AND METHOD OF PRODUCING THE SAME

BACKGROUND OF THE INVENTION

1. Field of the Invention

The invention is based on an exhaust gas sensor as generically defined in the main claim, and a method of producing the same.

2. Description of the Related Art

Exhaust gas sensors, particularly lambda sensors, are already known from, for example, DE-OS 2,265,309; these have a porous layer that covers the measuring electrode and is composed of a material that catalyzes the establishment of the gas equilibrium, which layer can also be, for example, a catalytically inactive, porous ceramic layer that contains finely-distributed precious metals. These precious metals, particularly from the platinum group, act as getters, that is, as collecting substances for pollutants from the exhaust gas that can be detrimental to the electrode function, for example lead, silicon, phosphorus, and zinc. At the same time, they catalyze the establishment of the thermodynamic equilibrium and thus fix the sensor control position close to the stoichiometric point, that is, at $\mu = 1$.

Furthermore, a number of elements of the periodic table and their oxides have already been proposed as getters for pollutants from the exhaust gas. For example, DE-OS 4,033,388 describes the use of mixed oxides consisting of at least one alkali metal oxide and one thermally stable oxide of an element having a valence of at least three, preferably from the IIIa, IIIb or IVb groups. However, getter substances on a nonprecious metal basis are insufficiently reactive, particularly at low and medium application temperatures between approximately 300° and 600° C. Within this temperature range the degree of pollution is especially high, because the pollutants can precipitate, whereas at high temperatures they can be removed with the measuring gas.

Therefore, for low and medium application temperatures highly-reactive getter substances on a precious metal basis must be used. The associated drawback of this is that the sensor control position is determined at the stoichiometric point, and can thus no longer be deliberately set.

It is an object of the invention to simultaneously ensure protection of the measuring element of an exhaust gas sensor against pollutants at low and medium temperatures, and to set the sensor control position in order to adapt it to the respective application, particularly to optimize engine power, fuel consumption, conversion rate of the catalytic converter, etc.

SUMMARY OF THE INVENTION

This object is attained with an exhaust gas sensor having the features of the main claim.

It is particularly advantageous to use getter substances on a basis of precious metals, precious metal oxides or precious metal alloys, because these are also highly reactive with respect to pollutants from the exhaust gas, even at low and medium temperatures in a range of approximately 300° to 600° C.

The sensor control position can advantageously be set as a function of the layer thickness and/or pore structure of the layer(s) placed in front and facing the exhaust gas. Moreover, the control position can be influenced with catalyst material that has been purposefully introduced into the layer(s) facing the exhaust gas.

In an advantageous manner, the layer facing the exhaust gas, which serves to set the control position, can be equipped with a protective layer against erosive and corrosive influences of the exhaust gas, which layer can likewise contain getter substances on a non-precious metal basis.

The finely-dispersed distribution onto the pore walls of the protective layer, and hence the reactivity of the getter material, can be improved by means of thermally treating the ceramic layer impregnated with precious-metal solutions or suspensions.

DESCRIPTION OF THE PREFERRED EMBODIMENTS

Figure 1:
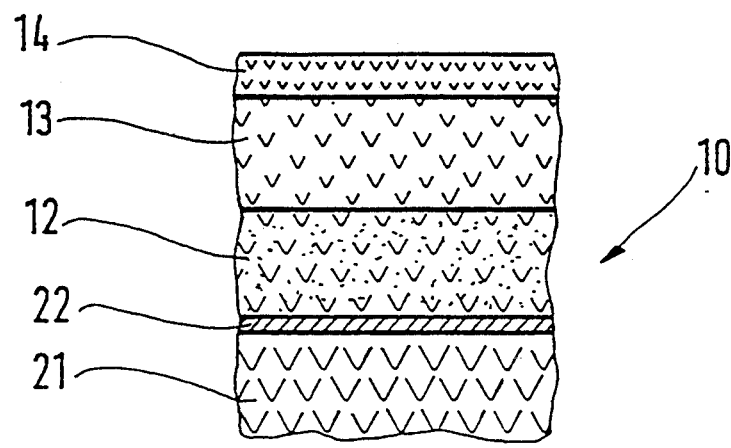

Embodiments of the invention are illustrated in the drawings and described in detail in the following description.

Figure 2:
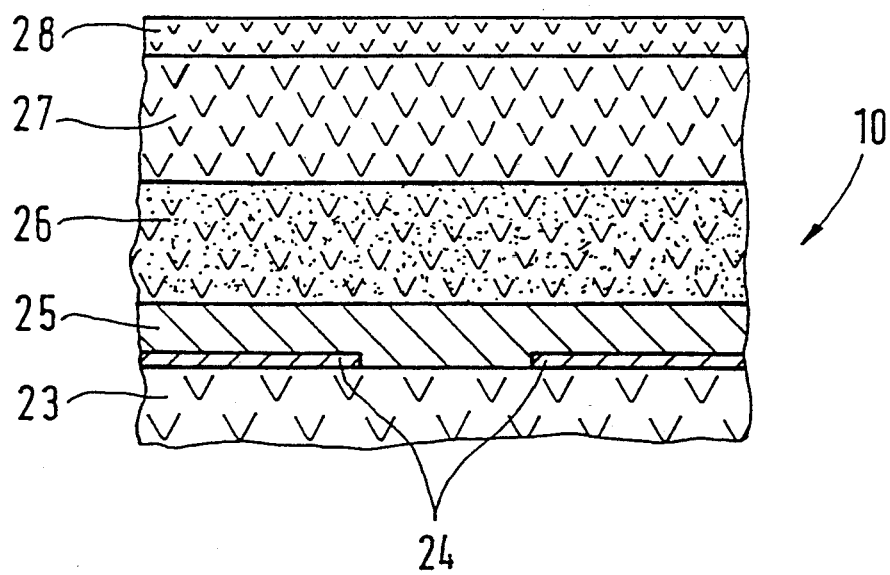

Shown are in:

FIG. 1 a section through an exhaust gas sensor in accordance with the invention that is configured as a lambda sensor, and FIG. 2 a section through an exhaust gas sensor configured as a solid-body sensor.

DESCRIPTION OF THE EMBODIMENTS

A first embodiment of the invention is schematically illustrated in FIG. 1. It is a lambda sensor, that is, an oxygen sensor, in accordance with the principle of galvanic oxygen concentration cells having a solid electrolyte. A precious-metal or precious metal-cermet measuring electrode 22 in accordance with DE-OS 2,852,638 is located on the fixed electrolyte 21 of zirconium dioxide stabilized with yttrium oxide, and a comparison electrode, not shown, is located on the opposite side; together these form the actual measuring element. The exhaust gas-side electrode reaction takes place at the three-phasic boundary of the solid electrolyte, electrode and measuring gas. A first ceramic layer 12 having getter substances that are distributed finely dispersed and are particularly on a precious-metal basis, is located on the measuring electrode 22. Adjoining the exhaust gas side is a second porous, ceramic layer 13 that serves to set the sensor control position. The layer 13 can be equipped with a protective layer 14 on the exhaust gas side.

To produce the exhaust gas sensor of the invention, the basis is, for example, a pre-sintered, small zirconium dioxide plate having a thickness of 0.6 to 0.8 mm as a solid electrolyte 21, and precious-metal or precious metal-cermet electrodes having a thickness of 5 to 15 $\mu$m, preferably 10 $\mu$m, are applied in accordance with methods known per se. In a known way, for example corresponding to DE-OS 2,852,647, an engobe layer having a thickness from 80 to 120 $\mu$m, preferably 100 $\mu$m, is then applied to the measuring electrode 22 as the first ceramic layer 12, for example by spraying or immersion into a ceramic slip that contains platinum powder distributed finely dispersed, and having a particle size preferably less than 1 $\mu$m and a proportion of preferably greater than 0.5 weight-%, preferably 3 weight-%. The layer system is dried and sintered at temperatures in a range of 1400 to 1500, preferably at 1450° C.

The ceramic layer 12 can also be applied and sintered on without the addition of a precious metal, and subsequently impregnated with, for example, 4% aqueous Pt-hexachloride solution and dried in air at 200° C.

A magnesium spinel layer 80 to 120 μm thick, preferably 100 μm thick, is subsequently applied as a second ceramic layer 13 using plasma-spraying technology. The now-completed coating is thermally aftertreated in the waste gas of a propane gas burner in a range of 500° to 950° C., particularly 900° C.

In an advantageous manner, the second ceramic layer 13 can be impregnated with a 0.14% rhodium-chloride solution to set the sensor control position.

In a variation of the method, following impregnation of the first ceramic layer 12, tempering in air takes place in a temperature range of 950° to 1050° C., preferably at 1000° C. In a further variation, it is provided to perform tempering in moist forming gas (90% $N_2$/10% $H_2$).

In order to impregnate the first ceramic layer 12, the platinum hexachloride can furthermore be replaced by a 2% rhodium-chloride solution. Tempering can also take place in air in a temperature range of 950° to 1050° C., preferably at 1000° C., in this variation.

In accordance with a further variation, the solid electrolyte 21 coated with electrodes is subjected to final sintering, and a spinel coating is applied as a first ceramic layer 12 in place of the engobe layer, the further method corresponding to the one described at the outset.

A protective layer 14 that can contain getter substances on a non-precious-metal basis, for example in accordance with DE-OS 4,033,388, can be applied to the second ceramic layer 13 serving to set the control position.

Finally, the platinum-hexachloride solution used to impregnate the first ceramic layer 12 can additionally contain water-soluble aluminum salts and lithium salts, preferably set at an $Al_2O_3/Li_2O$ mol ratio of 1:1.

The invention is not limited to lambda sensors in accordance with the potentiometric (Nernst) or amperometric (limiting current) principle, but is equally applicable to so-called solid-body gas sensors, that is, exhaust gas sensors whose solid-body properties change as a function of the concentration of one or a plurality of exhaust gas components. Among these are particularly the resistance sensors, for example on a $TiO_2$ or $SnO_2$ basis, as well as so-called semiconductor gas sensors, particularly on an Si basis.

FIG. 2 is a schematic, sectional representation through a resistance sensor that has electrodes 24 on an insulating substrate 23, as well as the actual measuring element, which in this part is a resistance layer 25, for example on a $TiO_2$ or $SnO_2$ basis. A first ceramic layer 26 having a getter effect and a second, exhaust gas-side ceramic layer 27, which serves to set the sensor control position, are in turn seated on the resistance layer 25.

The exhaust gas sensors of the invention according to FIGS. 1 and 2 thus have an at least two-layer ceramic coating 12, 13, 26, 27 with a first ceramic layer applied directly to the gas-sensitive measuring element and which also has a getter function with respect to pollutants from the exhaust gas, particularly at low and medium application temperatures, at which pollutants can precipitate particularly intensively and are not removed again from the measuring gas. The coating necessarily has at least one further ceramic layer disposed on the exhaust gas side, on the basis of which layer the sensor control position can be set. This second ceramic layer 13, 27 can be equipped with a getter protective layer 14, 28 on the exhaust gas side that is effective at high application temperatures.

Exhaust gas sensors having the at least two-layer coating on the measuring electrode achieve an improved exhaust gas quality in comparison to conventional sensors. In the silicon poisoning test executed with Si organic compounds that are soluble in fuel, with an Si concentration of 85 mg Si/l of fuel, the exhaust gas values for Co and $NO_x$ listed in the following table were obtained. Silicon can reach the vehicle exhaust gas as an impurity from the motor oil or from silicon seals (for example a cylinder head) or from silicon coatings. Examples of further known pollutants in vehicle exhaust gases are zinc and phosphorus (from the oil) and lead (from the fuel).

TABLE 1

| | Influence of Measuring Electrode Coating on the Attainable Exhaust Gas Quality | | | | | | | |
|---|---|---|---|---|---|---|---|---|
| | Coating | | | | Exhaust Gas Values (mg/l Exhaust Gas) | | | |
| | First Layer | | Second Layer | | New State | | After 30 hrs of Si poisoning | |
| Sensor type | Type | Getter | Type | Catalyst | CO | $NO_x$ | CO | $NO_x$ |
| 1 (Prior Art) | Mg-spinel plasma-sprayed | — | — | — | 1.9 | 0.39 | 2.5 | 1.9 |
| 2 (Invention) | $Al_2O_3/ZrO_2$—$Y_2O_3$ | Pt, 3 wt.-y. | Mg-spinel plasma-sprayed | — | 2.15 | 0.45 | 1.9 | 0.8 |
| 3 (Invention) | $Al_2O_3/ZrO_2$—$Y_2O_3$ co-sintered | Pt, 3 wt.-y. | Mg-spinel plasma-sprayed | Rh impregnation | 2.1 | 0.22 | 2.0 | 0.4 |

As can be seen from Table 1, the exhaust gas values for sensors of the prior art (sensor type 1) worsen considerably in continuous duty (test conditions: 30-hour silicon poisoning duration in comparison with the as-new state; the $NO_x$ value in particular clearly worsens. However, if the measuring electrode is provided with an at least two-layer coating, as proposed in accordance with the invention (sensor type 2), with a first layer serving as a getter and a second layer that faces the exhaust gas serving to set the sensor control position, significantly better exhaust gas values are achieved in continuous operation: in an experiment, a CO value was determined that was virtually unchanged in comparison to the as-new state, while the worsening in the $NO_x$ value was significantly less than the corresponding value for sensor type 1.

A further improvement in the attainable exhaust gas values can be achieved in accordance with the invention by means of impregnating the second layer facing the exhaust gas with catalysts that serve to set the sensor control position, such as rhodium (sensor type 3). These exhaust gas values of the sensor of the invention are still nearly as good after 30-hr Si poisoning as those of the prior sensor in the as-new state.

The function of the at least two-layer measuring electrode coating of the invention can be explained on the basis of the following considerations: a protective layer having finely-distributed getter substances, as could be applied in a known way to provide protection against pollutants from the exhaust gas that could be detrimental to the electrode function, acts as a diffusion barrier for the gaseous components of the exhaust gas. However, because the exhaust gas components vary greatly in their diffusion coefficients (see Table 2), this diffusion barrier causes a change in the relative concentration of the exhaust gas components on the measuring electrode in comparison to the exhaust gas: at the measuring electrode, the significantly faster-diffusing hydrogen will give a false indication of a richer mixture than is actually present in the exhaust gas, or, in other words, the measuring electrode will first display a stoichiometric air-fuel ratio ($\lambda=1$) when in fact an oxygen surplus exists in the exhaust gas, that is, when a lean mixture is present.

Table 2: comparison of the diffusion coefficients of the most important vehicle exhaust gas components in a temperature range of 400° to 800° (relative values):

| Exhaust gas component | Diffusion coefficient |
| --- | --- |
| $H_2$ | 100 (as reference variable) |
| $O_2$ | 13.5 |
| NO | 11 |
| CO | 12 |
| $C_3H_8$ | 4.5 |

In accordance with the invention, this "leanness offset" in the control position resulting from the different diffusion speeds of the individual exhaust gas components is now purposefully set to the respective application by means of a second layer placed in front on the exhaust gas side, and by means of setting the pore size and layer thickness of the second layer, or, in an advantageous manner, by impregnating the second layer with a pre-catalyst, for example rhodium. By means of the pre-catalyst, the exhaust gas components have already been extensively used up in the reaction before they traverse the coating acting as a diffusion barrier.

What is claimed is:

1. An exhaust gas sensor which is exposed to exhaust gas, comprising:

a measuring electrode; and a porous ceramic coating provided on the measuring electrode and comprised of at least two layers, a first porous ceramic layer which is provided on the measuring electrode and at least a second porous ceramic layer which is provided on the first porous ceramic layer and which is directly exposed to the exhaust gas, wherein the first porous ceramic layer contains getter substances for removal of substances that are harmful to the measuring electrode, and wherein the second porous ceramic layer is provided with one of a diffusion resistance or a catalytic effect relative to exhaust gas constituents such that, at the boundary of the first and second porous ceramic layers, a gas composition is present in use which is comprised of one of oxidizable or reducible gas constituents and which sets a control position for the exhaust gas sensor.

2. The exhaust gas sensor as defined in claim 1, wherein the measuring electrode is a solid electrolyte sensor having at least one catalytically active measuring electrode.

3. The exhaust gas sensor as defined in claim 1, wherein the measuring electrode is a resistance sensor having a resistance layer which is positioned between the first porous ceramic layer and the measuring electrode, and which has solid-state characteristics which change as a function of concentration of the exhaust gas constituents.

4. The exhaust gas sensor as defined in claim 1, wherein the first porous ceramic layer is provided with at least one getter substance selected from the group consisting of precious metals, precious-metal oxides, and precious-metal alloys.

5. The exhaust gas sensor as defined in claim 1, wherein the second porous ceramic layer contains at least one catalytic converter material for setting of a thermodynamic equilibrium in use.

* * * * *